United States Patent
Davis et al.

(10) Patent No.: US 6,603,052 B2
(45) Date of Patent: Aug. 5, 2003

(54) FLUID ABSORBENT ARTICLE FOR SURGICAL USE

(76) Inventors: John E. Davis, 9877 Hayfield Ct., Loveland, OH (US) 45140; Timothy P. Klonne, 10726 Weller Woods Dr., Cincinnati, OH (US) 45442

( * ) Notice: Subject to any disclaimer, the term of this patent is extended or adjusted under 35 U.S.C. 154(b) by 40 days.

(21) Appl. No.: 09/865,822

(22) Filed: May 25, 2001

(65) Prior Publication Data

US 2002/0177826 A1 Nov. 28, 2002

(51) Int. Cl.⁷ .......................... A61F 13/15; A61F 13/20; A61F 5/37; A61B 19/00
(52) U.S. Cl. ...................... 604/358; 604/365; 604/378; 604/383; 604/384; 604/385.23; 128/849
(58) Field of Search ................................. 604/358, 365, 604/378, 383, 384, 385.23; 128/849

(56) References Cited

U.S. PATENT DOCUMENTS

| | | |
|---|---|---|
| 2,128,118 A | 8/1938 | Burford |
| 2,923,298 A | 2/1960 | Dockstader et al. |
| 3,292,619 A | 12/1966 | Egler |
| 3,543,750 A | 12/1970 | Meizanis .................... 128/156 |
| 3,654,047 A | 4/1972 | Berkowitz ...................... 161/7 |
| 3,814,101 A | 6/1974 | Kozak ......................... 128/287 |
| 3,886,941 A | 6/1975 | Duane et al. ................ 128/287 |
| 3,929,135 A | 12/1975 | Thompson ................... 18/287 |
| 4,364,723 A | 12/1982 | Louis et al. ................. 425/384 |
| 4,508,256 A | 4/1985 | Radel et al. .................... 228/1 |
| 4,601,868 A | 7/1986 | Radel et al. ................. 264/504 |
| 4,839,216 A * | 6/1989 | Curro et al. ................. 428/134 |
| 4,846,813 A | 7/1989 | Raley ....................... 604/385.1 |
| 5,226,815 A | 7/1993 | Bowman ..................... 433/137 |
| 5,342,338 A * | 8/1994 | Roe ............................ 604/383 |
| 5,429,631 A * | 7/1995 | Grenier .................. 604/385.01 |
| 5,536,555 A | 7/1996 | Zelazoski et al. ........... 428/138 |
| 5,546,960 A * | 8/1996 | Billgren ...................... 128/849 |
| 5,762,643 A | 6/1998 | Ray et al. .................... 604/383 |
| 5,871,015 A | 2/1999 | Lofgren et al. ............. 128/849 |
| 5,873,868 A | 2/1999 | Nakahata .................... 604/383 |
| 5,906,879 A | 5/1999 | Huntoon et al. ............ 428/136 |
| 5,919,177 A | 7/1999 | Georger et al. ............. 604/367 |
| 5,925,026 A | 7/1999 | Arteman et al. ............ 604/383 |
| 5,993,430 A * | 11/1999 | Gossens et al. ........ 604/395.02 |
| 6,028,241 A * | 2/2000 | Armstead .................... 604/367 |
| 6,132,841 A | 10/2000 | Guthrie et al. .............. 428/132 |
| 6,202,250 B1 | 3/2001 | Kenmochi et al. ............ 15/231 |
| 6,228,462 B1 * | 5/2001 | Lee et al. .................... 428/132 |
| 6,248,097 B1 * | 6/2001 | Beitz et al. ............. 604/385.27 |
| 6,258,996 B1 * | 7/2001 | Goldman .................... 604/368 |

* cited by examiner

Primary Examiner—William C. Doerrler
Assistant Examiner—Filip Zec
(74) Attorney, Agent, or Firm—Wood, Herron & Evans, LLP

(57) ABSTRACT

A fluid absorbent article for surgical applications includes a top layer including an apertured film having a plurality of apertures formed therein. Each aperture includes a base and an apex with the aperture base oriented in an upper surface of the top layer and the apex positioned a depth below the base and upper surface. An absorbent layer includes an absorbent media positioned to underlie the top layer generally coextensive with the top layer and receive fluids passing through the top layer. The absorbent media is operable for dispersing and containing the fluid within the article. Bases of the apertures have a plurality of generally straight sides and are positioned with respect to the upper surface to present a plurality of different angles to fluid flowing on the upper surface to hinder and divert the fluid so that it more readily passes through the apertures to the absorbent layer. A bonding layer including a bonding media is positioned between the top layer and absorbent layer and is operable for bonding the apices of the apertures to the absorbent media generally over the length and width of those layers. The bonding media loses significant tack after curing and is applied and dimensioned to not interfere with the fluid flow of the article.

22 Claims, 2 Drawing Sheets

FLUID ABSORBENT ARTICLE FOR SURGICAL USE

FIELD OF THE INVENTION

This invention is directed to a fluid absorbent article generally, and specifically to a fluid absorbent article which is particularly suitable for use in surgical applications.

BACKGROUND OF THE INVENTION

Absorbent or absorptive structures are generally known and are utilized in various different articles of commerce. For example, some well known articles which utilize fluid absorbent components include disposable diapers, sanitary napkins, tampons, bed pads, surgical coverings, incontinence pads, towels, bandages, etc. Generally, such articles are single-use, disposable articles and have replaced permanent absorbent articles, which are designed to be laundered and re-used.

Depending upon the use of such articles, they will have various different constructions, although the articles often utilize common components having somewhat similar functions. Generally, such articles are meant to absorb fluids, such as bodily fluids, and retain those fluids within the article so that they may be cleanly disposed. The functions and qualities of the absorbent articles minimize mess and enhance clean-up and disposal of the bodily fluids. While the articles have similar absorbent qualities in common, their overall construction and components will generally be tailored to the specific use of the article.

In particular, medical articles or products, and especially those utilized in the surgical arena, such as surgical covers and drapes, must be able to absorb large amounts of fluids somewhat rapidly. Furthermore, they must be able to do so when draped over an object, thereby presenting a significantly sloped surface. Surgical drapes are most frequently draped over the patient proximate to the area where a surgical procedure is to take place. The absorbent media or components must provide rapid absorption of fluids associated with the surgical procedure, such as blood. Furthermore, the absorbent media also must have a relatively high fluid capacity and good integrity so that it does not degrade or fall apart during use.

In their basic design, surgical drapes have been simply a sheet of absorbent material. For conventional surgical drapes, the most commonly acceptable absorbent media is referred to as a cellulosic airlaid. Cellulosic airlaids are made of a plurality of loose cellulose fibers which are bonded together. One drawback of cellulosic airlaids is that the loose fibers may actually come loose during use of the surgical drape, and may thereby enter the wound. While the body may break down cellulose and dispose of it without intervention, it is still an undesirable feature. One approach to reducing the possibility of loose fibers is to simply bond the fibers more tightly. However, this results in lowering both the absorption rate of the media and also the absorption capacity. An additional approach, particularly for high-end or more expensive drapes, has been to utilize a netting component on a surface of the fibrous cellulose component to contain any fibers while maintaining a suitable absorption rate and capacity. Again, however, the netting and bonding media to attach it may also reduce the absorption rate.

Another possible solution for fibrous absorbent media proposed by the inventors, is to utilize a layer component having a series of apertures formed therein. Such a layer component is often referred to as an apertured film. While apertured films have desirable characteristics, they have also presented difficulties as well. Generally, apertured films utilize rows or lines of apertures which may provide rapid liquid flow therethrough when the film and any absorbent material are placed on a flat surface or are incorporated into a formed or shaped garment which acts to physically capture and contain the liquid. However, if the film is inclined and the fluid is rapidly applied, as is often the case when a surgical drape is positioned over a patient, most apertured films do not provide the desirable fluid flow therethrough for absorption by the absorbent media underneath. Existing apertured film designs do not present significant hindrance to the flow of fluid over the surface of the film. As a result, the fluid rolls over the surface and drips from the drape. This is certainly undesirable for an absorbent article. Consequently, certain apertured films have proven useful for generally flat applications or for use in formed or shaped garments, but have proven undesirable for a surgical drape or other surgical application.

Another issue with apertured films, which is also an issue with netting, is that the desired surface openness which allows fluid to flow through the film, also allows any bonding material or adhesive underneath the film to flow onto or be exposed to the surface of the film. Bonding material is positioned between the film and an absorbent layer underneath. For certain absorbent articles, such as diapers or feminine hygiene products, this openness is generally not a problem. Diapers and feminine hygiene products are usually formed to be used without modification, such as openings cut therein, and the bonding materials between the multiple layers may be marginally or peripherally positioned, keeping it out of the primary absorbent areas of the article. However, with surgical drapes, the apertured film should generally be bonded across the whole area of the absorbent media in order to maintain the bond everywhere when the drape is altered. For example, during surgery, one or more holes will be cut in the drape to allow access to the surgery site. The layers should not come apart at the hole and, therefore, the layers must be bonded together generally all over the drape.

Bonding over the entire area of the absorbent article has provided some challenges which are unresolved by the prior art. First, enough bonding material must be utilized to hold the apertured film to the absorbent media. However, such significant bonding may sometimes block the apertures and reduce the flow rate through the apertured film. Furthermore, the bonding media may detrimentally affect the distribution rate over the absorbent media. Still further, the fluid holding capacity of the absorbent media may be compromised.

Another issue which must be addressed by a surgical drape article is exposure of the surgical personnel, the patient, and surgery opening to the tacky bonding media. The openness of apertured films lends itself to a bleed-through of the bonding media or adhesive and subsequent exposure of the patient's skin to the tackiness of the bonding media. Furthermore, the tacky drape may be difficult to manipulate and position. This aspect should be minimized in a surgical drape, which will have bonding media throughout, rather than in marginal areas which might not significantly contact the skin.

Prior art surgical structures, particularly those using cellulose as an absorbent media, also have a tendency to swell in size upon the absorption of fluids. In the past, such swelling has broken the surface bond of the bonding media causing separation of the various layers of the drape when the drape absorbs fluid. Improving the bond by using a greater quantity of the bonding agent or adhesive is unacceptable because it causes a reduction of the fluid absorbency rate and reduces the overall fluid capacity of the article.

Accordingly, it is an objective of the invention to improve upon existing absorbent articles and particularly to provide an improved article for surgical applications.

It is another objective of the invention to improve the absorbent characteristics of a surgical article, such as a surgical drape, by reducing fluid flow off of the article, improving the distribution of fluid flow over the article and improving the fluid capacity of the article.

It is still a further objective to utilize an absorbent article having an apertured layer, wherein the integrity of the apertured layer is maintained to provide improved absorbent characteristics.

It is another objective to reduce tacky adhesives or bonding media which bleeds through the apertures of the apertured film while maintaining a sufficient bond between the layers, both when the absorbent media is wet and when it is dry.

These objectives and other objectives will become more readily apparent from the description of the invention hereinbelow.

SUMMARY OF THE INVENTION

The present invention is a unique combination of elements which provides a fluid absorbent article which is particularly suitable for surgical applications, such as for a surgical drape. The article is operable for absorbing a large amount of fluid, such as during a bloody surgical procedure, even when it is oriented at a significant slope with respect to a ground surface. The combination of elements operates to absorb and hold the fluid at a rapid rate, and may be positioned and modified, such as by cutting a hole therein, without compromising its absorbent qualities. To that end, the fluid absorbent article directed to surgical applications comprises a top layer, including an apertured film having a plurality of apertures formed therein. The apertures have bases and apices, wherein the base of each aperture is located in an upper surface of the top layer, and the apex is positioned at a depth below the base and the upper surface of the top layer. An absorbent layer, including an absorbent media, is positioned to underlie the top layer and to be generally coextensive therewith. The absorbent layer absorbs fluid passing through the top layer and disperses and contains those fluids.

In accordance with one aspect of the present invention, the bases of the apertures have a plurality of generally straight sides. In one embodiment, the aperture bases are pentagonal or hexagonal in shape. The apertures of the bases are positioned relative to the upper surface to present a plurality of different angles to fluid flowing over the upper surface. The different angles presented by the straight sides of the aperture bases hinder and divert the fluid so that it more readily passes through the apertures to the absorbent layer.

In accordance with another aspect of the present invention, a bonding layer, including a bonding media, is positioned between the top layer and absorbent layer. The bonding layer is operable for bonding the apices of the apertures to the absorbent media, generally over the length and width of those layers. In that way, the bonding layer secures the layers together, generally over the length and width of the fluid absorbent article. Since the bonding layer generally bonds only at the apices, the depth of the apertures and the thickness three-dimensional top layer are maintained. In one embodiment, the bonding media is applied between the layers in a plurality of strands. The strands generally have a width dimension which is less than the depth of the apertures in order to bond the top layer primarily at the apices of the apertures. Furthermore, the width dimension of the strands is also less than the average width dimension of the aperture apices, so that the bonding layer does not significantly interfere with the flow of fluid through the top layer. The bonding layer may be applied in a plurality of spiral strands having a diameter in the range of 1–12 inches, and preferably 3–4 inches.

In accordance with another aspect of the present invention, the bonding media has a tack after curing which is significantly reduced from its tack prior to curing. In that way, a suitable bond is created between the top layer and absorbent layer during formation of the fluid absorbent article. However, after curing, the tack of the bonding media is reduced over 60%, preferably over 70–75% from its tack prior to curing. The top layer may have an open area defined by the apertures in the upper surface of the layer in the range of approximately 15–35%. As such, the apertures expose the bonding media below. Because of the small dimensions of the strands, as well as the reduction in tack after curing, the finished fluid absorbent article does not have an undesirable tackiness. Simultaneously, the bonding layer still maintains a bond strength of at least 20 grams/inch, whether the fluid article is dry or wet from having absorbed fluid. The maintained bond strength, even when wet, is particularly desirable for a surgical drape, as the layers of the drape are bonded together over generally the entire area of the drape, rather than just marginal surfaces. As such, the bonding media, in some area of the drape, will always be exposed to fluid, and still must maintain strength to prevent separation of the layers at the absorbent area.

Therefore, the unique fluid absorbent article of the invention utilizes the combination of elements and properties which provides a desirable article, such as for surgical applications, and addresses the objectives set forth above and other objectives. The details of the invention and its particular advantages will be more readily understood from the Detailed Description of the Invention set forth hereinbelow.

BRIEF DESCRIPTION OF THE DRAWINGS

The accompanying drawings, which are incorporated in and constitute a part of this specification, illustrate embodiments of the invention and, together with a general description of the invention given below, serve to explain the principles of the invention.

DETAILED DESCRIPTION

Figure 1:
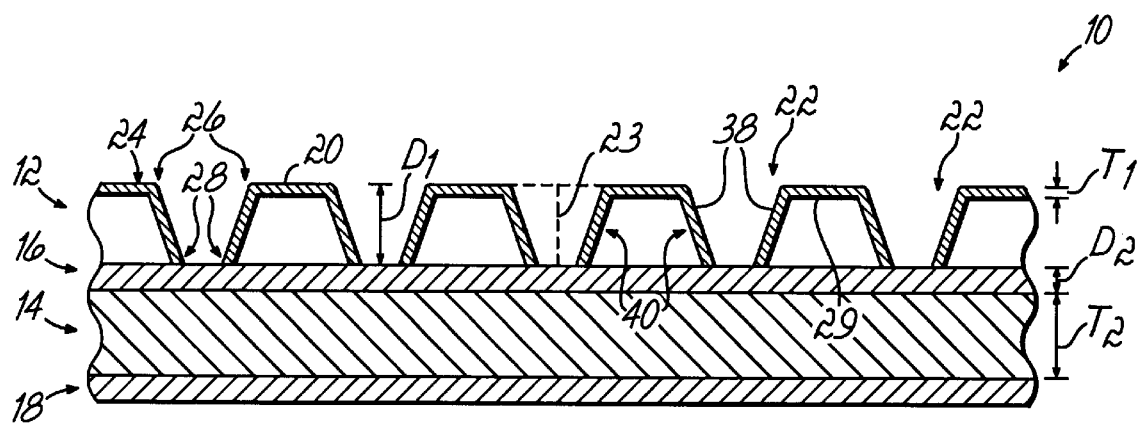
FIG. 1 is a side cross-sectional view of an absorbent article in accordance with the principles of the present invention.

FIG. 1 shows a partial cross-sectional view of a fluid absorbent article in accordance with the principles of the present invention. Article 10, which might be utilized, or example, in a surgical application, such as a surgical drape or cover, comprises a plurality of individual layers bonded together. Article 10 includes a top layer 12, an absorbent layer 14 underneath the top layer, and a bonding layer 16 positioned between the top layer and the absorbent layer. In one embodiment of the invention, an optional anti-static layer and/or barrier 18, such as an anti-static film, might be utilized, but is not necessary.

Top layer 12 includes an apertured film 20 having a plurality of apertures or capillaries 22 formed therein. Various different apertured films are known and are commercially available. The apertured film has a thickness $T_1$ generally between the apertures in the range of 0.5–5.0 mils. Preferably the thickness $T_1$ is approximately 1.0 mil. The thickness $T_1$ may also be maintained over the walls of the apertures 22, but the aperture walls may be thinner due to the process of producing those apertures from a film of a certain thickness. Film 20 defines an upper surface 24 and lower surface 29, and the apertures 22 extend downwardly from upper surface 24 toward absorbent layer 14. In one aspect of the invention, the apertures have a depth $D_1$ in the range of approximately 200–800 microns, which creates a three-dimensional thickness or loft for layer 12. In one embodiment, the depth is around 580 microns. The apertures 22 and their depth from upper surface 24 form a three-dimensional apertured film which may be made from a material such as polyethylene. In the present invention, one suitable apertured film 20 which has the desired characteristics for use in combination with the various components of the invention is commercially available from Tredegar, Richmond, Va., under the name Hex-Penta. The upper surface 24 of the apertured film 20 may be treated to enhance fluid flow through the apertures 22 in manners which are well known to persons of ordinary skill in the art.

Each aperture 22 is defined by a base 26 and an apex 28. The base is oriented generally in or proximate to surface 24 of the top layer 12. The apex is positioned at a pre-defined depth below the base which defines the depth $D_1$ of the aperture. As it may be readily understood, thin polyethylene film with the thickness of approximately 1.0 mil, is not particularly rigid, and therefore, apertures 22 formed therein will not have a rigid structure or an absolutely defined depth or dimension. Therefore, the dimension ranges and the dimensions of the apertures set forth herein are not absolute, but are based upon average dimensions of the different apertures 22. In accordance with one aspect of the invention, the depth of the apertures is not significantly compromised or reduced when the article is formed.

In accordance with another aspect of the present invention, the bases of the apertures have a plurality of generally straight sides, and the bases are positioned with respect to the upper surface to present a plurality of different angles to fluid which flows on the upper surface. The generally straight sides positioned at the plurality of different angles hinders and diverts fluid flowing across the top layer 12 so that it may more readily pass through the apertures 22 to the absorbent layer 14 below.

Figure 2:
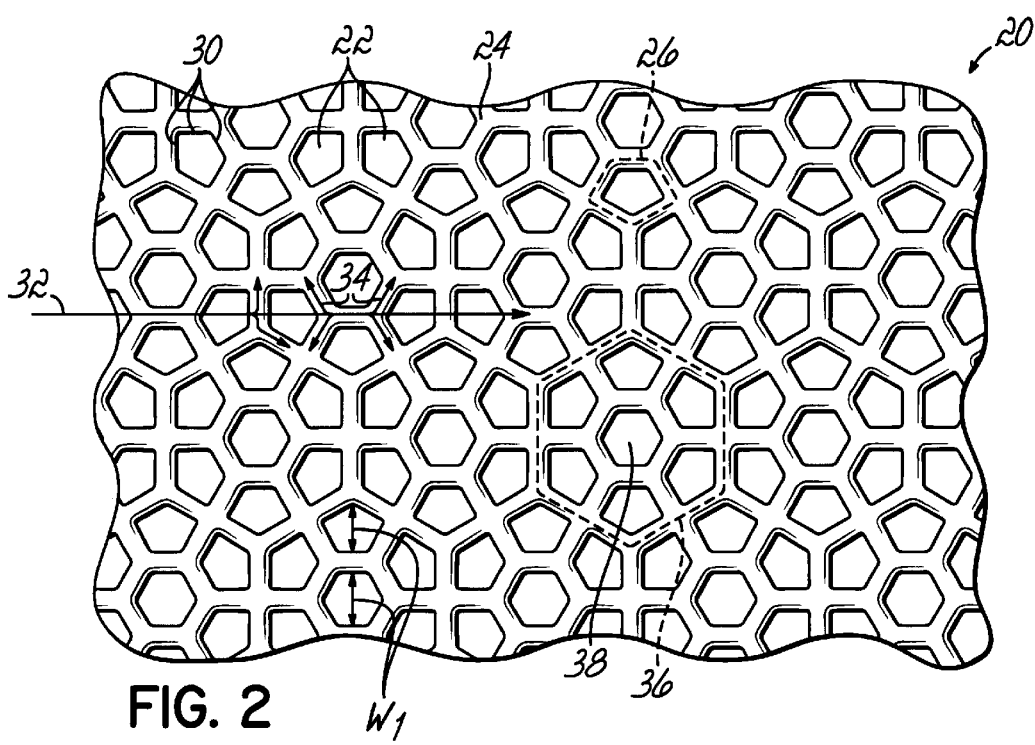
FIG. 2 is a partial top view of an apertured film utilized in one embodiment of the present invention.
Figure 3:
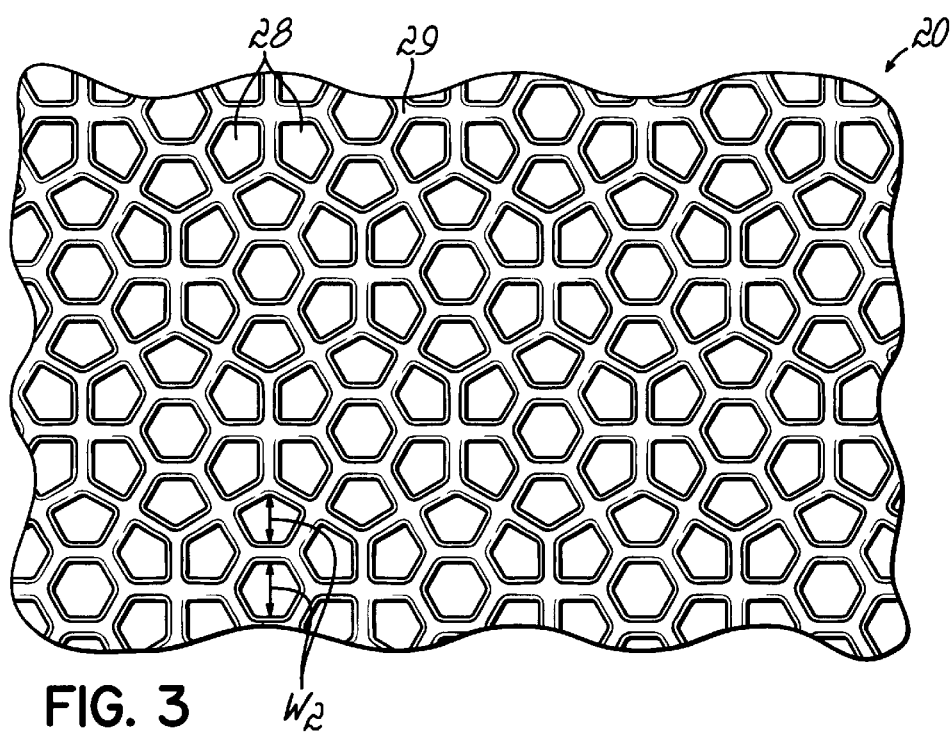
FIG. 3 is a bottom view of an apertured film utilized in one embodiment of the present invention.

FIGS. 2 and 3 are partial top and bottom views, respectively, of an apertured film 20 which may be used in accordance with one embodiment of the present invention. Specifically, FIGS. 2 and 3 show top and bottom views, respectively, of an apertured film available under the mark Hex-Penta, as discussed above. Aperture 20 has an upper surface 24 and a lower surface 29. A majority of the apertures 22 have a pentagonal shaped base 26 defined at the upper surface 24. As illustrated in FIG. 2, the base of each aperture has five generally straight sides 30, which define the base and its shape. The apertures are constructed and arranged such that fluid flowing on the upper surface 24 is hindered and diverted so that it more readily passes through the apertures to the absorbent layer. The bases of the apertures having the straight sides 30 are positioned with respect to the upper surface to present a plurality of different angles to fluid flowing on the upper surface to hinder and divert the fluid. Specifically, referring to FIG. 2, a flow of fluid taking the path as illustrated by reference arrow 32 will pass several different generally straight sides which are angled at different angles with respect to the path 32 of the fluid flow. The straight sides will have a tendency to divert the fluid, as illustrated by arrows 34, and thereby more efficiently direct the fluid to a greater number of apertures to pass therethrough and be absorbed. The unique shape of the apertures, and their arrangement on the top surface 24, in combination with the other components of article 10, have been found by the inventors to provide a desirable absorption rate and absorbent capability and capacity of the article 10. By diverting the fluid, the fluid flow is also somewhat hindered or slowed, so that it might be completely absorbed in the absorbent layer 14 before passing off the edge of the article. This is particularly desirable in surgical applications where blood may be flowing over the surface of the article and the article has a significant slope where it passes over the ends or sides of a patient on an operating table. The blood flow may be occurring at a rate greater than the absorption rate of layer 14. However, since the blood flow will be hindered and diverted by the features of the invention, greater absorbency can occur. Furthermore, the diversion prevents one spot or area from becoming over saturated and spreads out the fluid over the area of the article. Other features of the invention also ensure desirable fluid flow over the absorbent layer 14 once the fluid passes through the apertured film 20, as discussed further hereinbelow.

In one embodiment of the invention, the apertures are arranged in hexagonal groupings, as illustrated by the hexagon 36. To that end, a center aperture 38 has an hexagonal shape as well, and is surrounded by six apertures having pentagonal shaped bases. The hexagonal groupings are then stacked or arranged side-by-side, as illustrated in FIG. 2, so that the apertures cooperate to present multiple sides 30 at various angles to hinder and divert the fluid flow, as discussed above. As the apertures retard the fluid flow across the upper surface, and assist in redirecting the fluid from its original flow path, the amount of fluid that runs off article 20, possibly onto a surgery room floor in certain surgical applications, is reduced or eliminated, while the amount of fluid available to be presented to the absorbent layer 14 is increased.

Referring to FIG. 3, while the upper surface 24 is generally planar, the bottom surface 29 is defined by certain planary sections corresponding to the film between the apertures, as well as three-dimensional sections, as defined by the plurality of apertures. That is, on the bottom surface 29, the apertures essentially form protuberances wherein each protuberance defines an aperture with a depth $D_1$. While FIG. 3 shows the bottom surface 29 defining apertures with generally straight lines, the openings illustrated on the bottom surface 26 are the apices 28 of the apertures. Due to the slope of the aperture walls, as illustrated, the apices are generally smaller than the bases 26 in their average width dimension and will usually be less defined in shape than the bases. The loss of definition is usually due to the way in which the apertured films are formed and the flimsiness or non-rigidity of the thin film 20. In one embodiment, the apertures, at their base, have an average width dimension in the range of approximately 30 to 60 mils. Referring to FIG.

2, $W_1$ indicates two possible widths of the pentagonal shaped aperture and a hexagonal shaped aperture. The average width $W_1$ for one embodiment of the invention is in the range set forth above. Because of the various different widths which might be measured for the five- and six-sided apertures, depending upon where the measurement occurs, the apertures may be considered to have an overall average width in the range above. In a preferred embodiment, the inventors have found that width dimension to be, on average, approximately 46 mils. The apices 28 are generally similarly configured and will have an average width dimension in the range of approximately 30 to 45 mils. As illustrated in FIG. 1, the sides 40 of the apertures taper or slope downwardly from the base 26 to the apex 28. With respect to a reference line 23 which is perpendicular to the plane of the article, the range of that slope, from line 23 is from approximately 3 to 30 degrees.

As will be readily understood by a person of ordinary skill in the art, the various different dimensions of the apertures may be modified without deviating from the scope of the invention. The inventors have determined that the top layer having an open area, or apertured area, at least in the range of 15% to 35%, and preferably at least 20% has the desired fluid flow rate therethrough. That is, the open area defined by the apertures is at least 20% of the area of the upper surface 24 of the top layer 12.

Absorbent layer 14 includes an absorbent media which is positioned to underlie the top layer 12 generally coextensive with the top layer. The absorbent layer 14 receives fluids passing through the top layer 12 and is operable for dispersing and containing the fluid within the article. The absorbent media must accomplish at least two functions. First, it must be able to quickly absorb the fluid. Secondly, it must be able to contain or hold a large quantity of fluid so that it does not become saturated quickly and allow unabsorbed fluids to run off the upper surface 24. The absorbent media might be any number of known absorbent materials, including fibrous material, non-woven fabric, and woven fabric. The fibrous material might be selected from the material group consisting of polyester, polyolefins, acrylics, rayons, cotton, cellulose materials, and blends of those same materials. In a preferred embodiment of the invention, the absorbent media is a loosely bonded cellulosic fiber. One suitable cellulosic fiber is commercially available as LDL-100L available from Concert Industries, Quebec, Canada.

In a cellulosic fiber media, the fluid enters the absorbent layer 14 between the voids around the fibers of the absorbent media. If the fibers are hydrophilic, the fluid will wet out or cling to the surface of the fibers. If the fibers are absorbent, fluid will enter the fiber and it will swell. If the fibers are made of what is referred to as "super-absorbers" those fibers will be able to absorb large quantities of fluid. Once the area immediately under the application point starts to become saturated, the fluid begins to flow across the surface of the saturated absorbent media to an unsaturated area. This flow will continue until the fluid either finds an unsaturated area or flows off of the edge of the article 10. A secondary flow of fluid occurs through the fibers away from the application point, due to a wicking effect. The distance between the fibers, the distribution of the fibers, and the bonding method used to secure the fibers together will all affect the speed at which fluid can move laterally (wicking) through the absorbent media. The capacity of the absorbent media will generally be affected by all of the same factors. The high fluid capacity of cellulosic fibers makes cellulose fiber media desirable in the present invention. While hydrophilic synthetic fibers may approach cellulosic fibers' performance, the cellulose's ability to absorb liquid makes it desirable due to its high fluid capacity. Furthermore, cellulose is desirable for the surgical applications to which the present invention is primarily directed. While it is not desirable for any foreign material to enter a surgical opening, the body is able to break down cellulose and dispose of it without intervention. Another fiber, such as one considered a "super-absorber" is a less certain choice with respect to its long term effects if it were trapped in the human body. The absorbent layer 14 has a thickness $T_2$ which is appropriate for the application. The thickness will often be dictated by the desired absorbency which is measured in grams of fluid per gram of material. For one embodiment of the invention, an absorbency in the range of 7–13 grams of fluid per gram of material, and preferably around 10, is suitable. Suitable absorbent material has a weight in the range of 60–130 grams/square meters.

The bonding layer 16, including a bonding media, is positioned between top layer 12 and the absorbent layer 14. The bonding layer is operable for bonding the two layers 12, 14 together into a unitary article, and is also operable for maintaining that unitary structure regardless of whether that article is wet or dry. As such, even upon absorbing fluids, such as bodily fluids and blood in a surgical operation, the fluid absorbent article 10 of the invention, and specifically the layers thereof, remain bonded together. In accordance with the principles of the present invention, the particular type of bonding media, and the way in which it is utilized to bond the top layers and the absorbent layers together, in accordance with the principles of the present invention, provides desirable characteristics of the inventive fluid-absorbent article, and particularly provides desirable characteristics for use in the surgical arena, such as for a surgical drape or cover.

Specifically, in accordance with one feature of the bonding layer 16, the bonding media is applied between the layers in a plurality of strands. The strands are made and formed to have a width or depth dimension $D_2$ which is less than the depth $D_1$ of the apertures of the apertured film 20. Therefore, the top layer is bonded to the absorbent layer primarily at the apices of the apertures, as illustrated in FIG. 1. In that way, the depth dimension $D_1$ of the apertures is generally maintained intact and the apertures are not collapsed. The apertured film 20 retains its three-dimensional shape and ensures a plurality of open apertures 22 for absorbing fluid and directing it efficiently to the absorbent layer 14. Therefore, the depths of the apertures 22 (i.e., in the Z direction) are maintained. This feature of the invention provides several desirable qualities, particularly for a surgical drape.

Firstly, the apertures bonded primarily at the apices creates a series of flow channels on the surface of the absorbent layer 14 below top layer 12. The apertures form a grid above layer 14, as shown in FIGS. 1 and 3, through which the fluid must travel as it is being absorbed by the absorbent layer 14. Pillar structures formed by the apertures between upper surface 24 and the top surface of the absorbent layer 14 divert and slow the fluid on the absorbent layer 14 and increase the absorbency of the layer so that the fluid does not pass out of the article 10, such as at an edge of the article. Furthermore, the grid directs fluid from a saturated area to a less-saturated area for better absorbency and higher fluid capacity in the article.

Another feature provided by the invention is also due to the top layer 14 maintaining its three-dimensional structure. The top layer 12, due to the three-dimensioned quality of the apertured film 20, provides a cushioning effect, and in turn, provides a gripping quality to items which are laid on the article 10. As may be appreciated, during surgery, various surgical instruments, such as scalpels and clamps, are utilized. As such, surgeons or other medical staff may place those instruments on the article 10 proximate to the surgery site during use. In prior art surgical drapes and covers, the upper surface is relatively slick, and thus there is a tendency for the surgical implements to simply slide off of the drape and onto the floor. As such, such instruments can no longer be used, or must be sterilized before being used. The present invention, in effect, grips the surgical implements and allows a surgeon to keep them handy and proximate to the surgical site without significant fear that they will slide onto the floor.

Also because of the three-dimensional nature of the layer 12, surface 24 tends to stay relatively dry, even after the fluid is absorbed. The apertures form generally a one-way capillary action wherein fluid goes into the apertures to be absorbed, but does not significantly flow back out.

In accordance with another aspect of the present invention, the bonding media is positioned between the top layer and absorbent layer, generally over the length and width of those layers or generally over the areas defined by the article 10. In that way, the bonding layer secures the layers together generally over the length and width of the entire fluid absorbent article. As noted above, a fluid absorbent article utilized in surgical environments often has to be modified or cut to allow access to a surgical site. That cut may occur anywhere within the article. As such, the present invention utilizes a bonding media generally over the length and width (area) of the layers so that the layers will not simply separate, no matter where the hole or opening is cut. It should be noted that the terminology "over the length and width of the layers" or "over the area" of the article does not imply that the bonding layer is a solid layer over its entire area. Rather, as discussed hereinbelow, in one embodiment, the bonding media is applied in a plurality of strands and is applied in a desired pattern, such as a circular pattern so that the layers 12, 14 are bonded together generally over the entire area of the article. Therefore, while there will be significant area between the top layer and absorbent layer which does not have the bonding media therebetween, the pattern and application of the bonding media over the length and width of the fluid absorbent article ensures that any given discrete area between the strands or bonds is small, given the overall area of the article. Also, there are no large non-bonded areas or unbonded margins of the article 10. As such, depending upon where a hole is cut in the article, the top layer and absorbent layer will generally be held together by the bonding layer.

In accordance with another aspect of the present invention, the bonding layer does not interfere with the operation of the apertures and the absorbent quality of absorbent layer 14. To that end, each of the apices 28 of the apertures 22 have an average width dimension, such as the width dimension indicated as $W_2$ in FIG. 3. The bonding media is applied between the layers in a plurality of strands and the strands have a minimum width dimension $D_2$ that is less than the average width dimension $W_2$ of the aperture apices 28. In that way, the bonding layer does not significantly interfere with the flow of fluid through the top layer and into the absorbent layer. That is, the bonding layer does not significantly block the apertures, such as may occur if the bonding layer 16 were a continuous sheet of bonding media, or if the strands of bonding media had a dimension larger than the width dimension of the aperture apices.

In one embodiment of the invention, the strands have a width in the range of approximately 5 to 25 mils, and preferably are less than 10 mils in width or diameter, so that they do not block the film apertures. In some applications, the strands are extruded to be somewhat cylindrical in shape and thus, the width of any particular strand would be essentially the diameter dimension of the circular cross section of the strand. In any case, the widest width dimension of the strand is below the average width of either the base $W_1$ or apex $W_2$ of the aperture.

In accordance with another aspect of the present invention, the bonding media has a tackiness or tack characteristic when it is applied that is sufficient to ensure that the top layer is secured to the absorbent layer. In that way, the bonding media achieves a desirable bond when the apertured film 20 and the absorbent media of layer 14 are brought together. However, to reduce article tackiness which occurs due to the exposure of the bonding layer through the apertures, the tackiness of the bonding media diminishes after it is applied. The bonding media of layer 16 has a tackiness after curing which is generally reduced over 60% from its tackiness prior to curing, and preferably is reduced over 70–75% from its tack prior to curing. Due to the open nature of the apertured film 20, some exposure of the bonding media of layer 16 to the top surface 24 is inevitable. Therefore, the minimal tackiness after curing provided by the present invention allows the article 10 to be manipulated easily without clinging to the hands or fingers of the person, such as medical personnel manipulating the article for a surgical procedure. Furthermore, the bonding media should be able to pass any required medical skin contact or standards required by medical product manufacturers, since the skin of a patient may also be exposed to the bonding material, due to the openness of the apertured film 20.

In accordance with another aspect of the present invention, the bonding media of layer 16 has a minimum bonding strength of at least approximately 20 grams/inch. The bond strength is maintained even when the absorbent media is saturated by fluids. In an absorbent media, such as cellulose, the media will swell when it absorbs fluid. In prior art surgical drapes, the swelling has been sufficient to break the surface bond of many conventional bonding media and adhesives. Using a greater quantity of the bonding media or adhesive to achieve an encapsulation or mechanical lock of the fibers of the absorbent media with the bonding media as a possible solution is not acceptable, because it causes a reduction in the fluid absorbency rate and a reduction in the overall capacity of the fluid-absorbent article 10. The bonding media of the present invention, as applied in the desired circular pattern of strands, as discussed below, provides a bond strength of at least 20 grams/inch, either wet or dry. One suitable bonding media is a pressure-sensitive adhesive, such as HL-1500X available from H. B. Fuller Company of St. Paul, Minn., which has been found to lose 70–75% of its tack on the surface within a curing time of 24 hours. Such a pressure-sensitive adhesive is a crystalline hot melt which may be applied by a number of different application methods, such as fine line, spiral spray, control coat and melt blown.

An anti-static film 18, such as a known anti-static polyethylene film might be utilized on the side of the article opposite top layer 12, and might be bonded thereto by a suitable adhesive.

Figure 4:
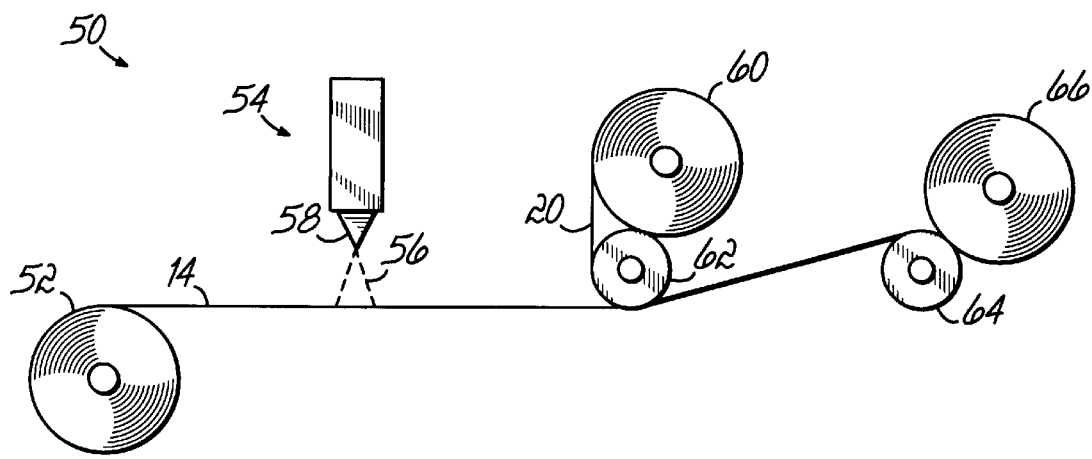
FIG. 4 is a schematic view of the process for producing an absorbent article in accordance with one aspect of the present invention.

Turning to FIG. 4, one suitable process for manufacturing the inventive fluid absorbent article is set forth. Specifically, system 50 utilizes a roll 52 of an absorbent media for making absorbent layer 14. The absorbent media from roll 52 is unwound and is passed through a bonding station 54. At the bonding station, a bonding media 56, such as a pressure-sensitive adhesive, is applied to a side of the absorbent media. In one embodiment of the invention, the bonding media is applied in a plurality of strands, by a spiral spray. The adhesive strands are drawn down to a smaller size, such as from an initial 20 mil diameter strand to a strand which is 10 mils or less. This may be done by using a spiral spray applicator, which is well known to a person of ordinary skill in the art, which has a custom-designed air distributor cap that causes a high velocity of hot air to create a broad cyclone effect or swirl. Using the broader cyclone or swirl, and positioning the nozzle 58 of the bonding station approximately 6–7 inches above the layer of absorbent media, rather than the traditional 1–3 inch spirals, spiral patterns are achieved in accordance with the principles of the present invention, and are sized from 1 inch to 12 inches in diameter. Preferably, 3–4 inch diameter spirals are utilized in a desirable embodiment. After the bonding media is applied, the apertured film 20 is then rolled from a roll 60 and is brought into contact with the bonding material at roller 62. The article with the top layer 12 bonded to the absorbent layer 14 then passes to another roller 64. In accordance with one aspect of the present invention, the pressure applied prior to the bonding layer or adhesive curing should not flatten the apertures in the film 20. The pressure is provided by the lay on roller 64. The pressure applied by roller 64 is 2.8 pli or less. The finished product is then rolled upon another roll 66.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details representative apparatus and method, and illustrative examples shown and described. Accordingly, departures may be made from such details without departure from the spirit or scope of applicant's general inventive concept.

What is claimed is:

1. A fluid absorbent article for surgical applications comprising:
   a top layer including an apertured film having a plurality of apertures formed therein, each aperture including a base and an apex with the aperture base oriented in an upper surface of the top layer and the apex positioned a depth below the base and upper surface;
   an absorbent layer including an absorbent media positioned to underlie the top layer generally coextensive with the top layer and receive fluids passing through the top layer, the absorbent media operable for dispersing and containing the fluid within the article;
   bases of the apertures having a plurality of generally straight sides and positioned with respect to the upper surface to present a plurality of different angles to fluid flowing on the upper surface to hinder and divert the fluid so that it more readily passes through the apertures to the absorbent layer;
   a plurality of the apertures having a pentagonal shaped base and being arranged in hexagonal groupings;
   a bonding layer including a bonding media positioned between the top layer and absorbent layer and operable for bonding the apices of the apertures to the absorbent media generally over the length and width of those layers, to secure the layers together generally over the length and width of the fluid absorbent article while generally maintaining the depths of the apertures of the top layer.

2. The fluid absorbent article of claim 1 wherein the bonding media has a tack after curing which is reduced over 60 percent from its tack prior to curing.

3. The fluid absorbent article of claim 1 wherein said bonding media is applied between the layers in a plurality of strands, the strands having a width dimension less than the depth of the apertures of the top layer for bonding the top layer to the absorbent layer primarily at the apices of the apertures.

4. The fluid absorbent article of claim 1 wherein said apertures have a depth in the range of 200 to 800 microns.

5. The fluid absorbent article of claim 1 wherein the apertured film, generally between the apertures, has a thickness in the range of 0.5 to 5 mils.

6. The fluid absorbent article of claim 1 wherein said aperture apices have a minimum width dimension, the bonding media being applied between the layers in a plurality of strands, the strands having a width dimension less than the minimum width dimension of the aperture apices so that the bonding layer does not significantly interfere with the flow of fluid through the top layer.

7. The fluid absorbent articles of claim 1 wherein said aperture apices have an average width dimension in range of approximately 30 to 45 mils.

8. The fluid absorbent articles of claim 1 wherein said aperture bases have an average width dimension in range of approximately 30 to 60 mils.

9. The fluid absorbent article of claim 1 wherein said apertures define an open area over the upper surface in the range of approximately 15 to 35 percent.

10. The fluid absorbent article of claim 1 wherein said bonding layer creates a bond strength of at least approximately 20 grams/inch.

11. The fluid absorbent article of claim 1 wherein said bonding media is applied between the layers in a plurality of strands wound in spirals, the spirals having a diameter in the range of approximately 1 to 12 inches.

12. The fluid absorbent article of claim 1 wherein said bonding media is applied between the layers in a plurality of strands, the strands having a width in the range of approximately 5 to 25 mils.

13. The fluid absorbent article of claim 1 wherein the absorbent media is selected from the material group consisting of polyester, polyolefins, acrylics, rayons, cotton, cellulose materials and blends of those materials.

14. A fluid absorbent article for surgical applications comprising:
   a top layer including an apertured film having a plurality of apertures formed therein, each aperture including a base and an apex with the aperture base oriented in an upper surface of the top layer and the apex positioned a depth below the base and upper surface:
   an absorbent layer including an absorbent media positioned to underlie the top layer generally coextensive with the top layer and receive fluids passing through the top layer, the absorbent media operable for dispersing and containing the fluid within the article;
   a bonding layer including a bonding media positioned between the top layer and absorbent layer and operable for bonding the apices of the apertures to the absorbent media generally over the length and width of those layers, to secure the layers together generally over the length and width of the fluid absorbent article while generally maintaining the depths of the apertures of the top layer, the bonding media having a tack after curing which is reduced over 60 percent from its tack prior to curing.

15. The fluid absorbent article of claim 14 wherein said bonding media is applied between the layers in a plurality of strands, the strands having a height dimension less than the depth of the apertures of the top layer for bonding the top layer to the absorbent layer primarily at the apices of the apertures.

16. The fluid absorbent article of claim 14 wherein said apertures have a depth in the range of 200 to 800 microns.

17. The fluid absorbent article of claim 14 wherein the apertured film, generally between the apertures, has a thickness in the range of 15 to 125 microns.

18. The fluid absorbent article of claim 14 wherein said aperture apices have a minimum width dimension, the bonding media being applied between the layers in a plurality of strands, the strands having a width dimension less than the minimum width dimension of the aperture apices so that the bonding layer does not significantly interfere with the flow of fluid through the top layer.

19. The fluid absorbent article of claim 14 wherein said apertures define an open area over the upper surface in the range of approximately 15 to 35 percent.

20. The fluid absorbent article of claim 14 wherein said bonding layer creates a bond strength of at least approximately 20 grams/inch.

21. The fluid absorbent article of claim 14 wherein said bonding media is applied between the layers in a plurality of strands wound in spirals, the spirals having a diameter in the range of approximately 1 to 12 inches.

22. The fluid absorbent article of claim 14 wherein said bonding media is applied between the layers in a plurality of strands, the strands having a width in the range of approximately 5 to 25 mils.

* * * * *